United States Patent [19]
Calomiris

[11] Patent Number: 6,010,869
[45] Date of Patent: *Jan. 4, 2000

[54] METHOD TO COLLECT AND RECOVER MICROORGANISMS FROM ENVIRONMENTAL SAMPLES

[75] Inventor: Jon J. Calomiris, Arnold, Md.

[73] Assignee: The United States of America as represented by the Secretary of the Air Force, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 09/121,398

[22] Filed: Jul. 23, 1998

[51] Int. Cl.⁷ .............................. C12Q 1/24; B03D 3/00; C12N 1/02; C01B 15/16
[52] U.S. Cl. ..................... 435/30; 435/30; 435/288.6; 435/308.1; 210/696; 210/697; 209/5; 423/314
[58] Field of Search ................... 435/30, 803, 288.6, 435/308.1; 423/314; 208/425, 13; 210/696, 697; 209/5

[56] References Cited

U.S. PATENT DOCUMENTS

| | | | |
|---|---|---|---|
| 3,898,160 | 8/1975 | Finley | 210/696 |
| 4,717,660 | 1/1988 | Schulte | 435/30 |
| 5,089,142 | 2/1992 | Turunc | 210/728 |
| 5,215,575 | 6/1993 | Butler | 75/744 |
| 5,556,643 | 9/1996 | Bohanon et al. | 424/602 |

OTHER PUBLICATIONS

Taylor et al. Microscope, 28, pp. 47–49. (1980).
Holben et al. Applied and Environmental Microbiology, 54 (3), pp. 703–711. (Mar. 1988).
Katayama et al. Soil Science and Plant Nutrition, 44 (2), pp. 245–252. (Jun. 1998).

*Primary Examiner*—Ralph Gitomer
*Assistant Examiner*—Marjorie A. Moran
*Attorney, Agent, or Firm*—Charles E. Bricker; Thomas L. Kundert

[57] ABSTRACT

Presented herein is an improved method to collect and recover microorganisms from environmental samples. The method of this invention comprises the steps of (a) obtaining a sample for testing and, optionally, suspending the sample in a suitable liquid, (b) amending the sample with sodium hexametaphosphate and, optionally, centrifuging the sample to remove solid sediments, insoluble salts, inert materials, and the like, (c) centrifuging the sample through a separation column amended with sodium hexametaphosphate, and (d) recovering the microorganism-containing material remaining above the column for analysis.

4 Claims, No Drawings

METHOD TO COLLECT AND RECOVER MICROORGANISMS FROM ENVIRONMENTAL SAMPLES

RIGHTS OF THE GOVERNMENT

The invention described herein may be manufactured and used by or for the Government of the United States for all governmental purposes without the payment of any royalty.

BACKGROUND OF THE INVENTION

This invention relates to a method for concentrating and recovering microorganisms from difficult-to-separate samples, particularly environmental samples, for the purpose of their analysis or identification.

Existing protocols for detection of microorganisms present in natural environments are, in general, cumbersome, time consuming, or inadequate with respect to sensitivity or accuracy. Traditionally, environmental samples are processed to recover and cultivate targeted organisms. These organisms are then screened to verify identity. Cultivation methods usually require extensive incubation periods and a variety of tests may be needed to identify targeted organisms. Antibody-based detection systems, which were developed in the 1970s, are rapid but suffer from the possible generation of false positive signals. While DNA-based detection systems developed in the 1980s are accurate and rapid, their use for detection is limited by interferences imposed by substances present in environmental samples. Consequently, DNA-based detection requires sample treatment to ensure reliable detection of microorganisms. Reported methods for processing environmental samples to allow DNA-based detection of microorganisms typically involve release of DNA from the microorganisms, while still suspended in the sample, and subsequent isolation and purification of the released DNA. These methods require many steps, are time consuming, employ caustic and toxic chemicals, generate low yields of DNA, and expose the released DNA to environmental substances which may adversely affect DNA integrity.

Environmental samples such as soil, sewage, and surface water are complex mixtures which are heterogeneous in both their solid and soluble components. In composition, the samples sometimes contain high concentrations of solid sediments, colloids, emulsions, soluble and insoluble salts, biopolymers, biodegraded debris, inert materials and contaminating industrial and natural chemicals. The heterogeneity and complexity of environmental samples can prevent or invalidate direct detection methods. Microorganisms can adhere to particulates, rendering the microorganisms inaccessible to detection by conventional approaches which rely on liquid filtrate samples. Also chemicals and solutes contained within the samples can interfere or inhibit test methods. Sample coloration, for example, can obstruct test results when colors are part of the assay.

Detection of microorganisms and/or their products is complicated by the fact that in many instances, sample materials contain only small numbers of microorganisms ($10^2$ to $10^5$ cells/gm). Further, in many cases the microorganisms do not comprise a single strain or even a single genus but are a diverse collection of many different types of organisms. For these reasons, detection requires highly sensitive methods possessing broad spectrum specificity or a means of selecting specific organisms. Because of the requirements of both high sensitivity and broad spectrum specificity, detection approaches such as immunoassays directed toward the cells or their products are subject to chemical interferences.

To circumvent these problems, some manner of sample treatment has been typically required to concentrate the small numbers of organisms present in field sample materials and to free them from interfering materials which prevent analysis or cause inaccurate or false results. Generally, treatment processes can involve centrifugation, membrane filtration or chemical precipitation steps.

Solution gradients or density gradients are utilized in biochemical research to separate macromolecules such as proteins, DNA and RNA, and larger aggregates such as viruses and cells.

Solution gradients usually utilize a solute of varying concentrations to aid in the separation of particles. Examples of appropriate solutes are: sucrose, CsCl, Percoll™ (colloidal silica coated with polyvinyl pyrrolidone), ficoll (a copolymer of sucrose and epichlorohydrin), metrizamide (3-acetylamino-5-N-methyl-acetylamino-2,4,6-triiodobenzoyl-glucosamine), Nycodenz™, sodium acetate, glycerol and mixtures thereof. Particles are separated either by their velocity of sedimentation in a centrifugal field, or by their density in a centrifugal field if there is an isopycnic point within the solution column in the tube. Faster, or denser particles will appear lower in the tube.

After the sample has been subjected to centrifugation, the particles are recovered for analysis. Fractionation methods and apparatus used to recover the sample in the gradient may involve the transfer of the entire gradient or certain layers or bands of the solution gradient to other vessels. It is often desired to extract only desired bands from the solution gradient for electron microscopy, liquid scintillation or gel electrophoresis.

The Membrane Filter (MF) method utilizes micropore filters through which samples are passed so that the bacteria are retained on the surface of the filter. This method is often used when bacterial populations are very small, and a large sample is needed to get adequate numbers. The filter is then placed on the surface of a chosen medium, incubated, and the bacterial colonies growing on the membrane filter surface are counted and evaluated. This method is widely used and provides good results when combined with proper reagents and media.

It is an object of the present invention to provide an improved method to collect and recover microorganisms from environmental samples.

Other objects and advantages of the present invention will be apparent to those skilled in the art.

SUMMARY OF THE INVENTION

In accordance with the present invention there is provided an improved method to collect and recover microorganisms from environmental samples. The method of this invention comprises the steps of (a) obtaining a sample for testing and, optionally, suspending the sample in a suitable liquid, (b) amending the sample with sodium hexametaphosphate and, optionally, centrifuging the sample to remove solid sediments, insoluble salts, inert materials, and the like, (c) centrifuging the sample through a separation column amended with sodium hexametaphosphate, and (d) recovering the microorganism-containing material remaining above the column for analysis.

DESCRIPTION OF THE INVENTION

Material containing microorganisms may be obtained, inter alia, from animal tissues, suspensions of microorganisms, blood, urine, water, beverages, patient exudates, air or fuel suspected of containing microorganisms, and food or other environments. The procuring of a sample of an environment and its subsequent storage prior to assay may be carried out by any appropriate method known in the art. The size of the sample is controlled by the sensitivity and range of the means used to measure the microorganisms present in the sample. The sample, if not already in aqueous form, may be suspended in sterile water, buffer or saline solution.

The sample is then amended with sodium hexametaphosphate and, optionally, centrifuged to remove solid sediments, insoluble salts, inert materials, and the like. This may be performed by centrifugation at a force sufficient to result in a centrifugate having a lower layer substantially free from microorganisms and an upper layer (supernatant) substantially free from non-microorganisms. This is preferably carried out at a force from about 150 to 250 multiples of gravity. Centrifugation may not be necessary if the sample separates on its own.

After this separation, the supernatant containing microorganisms is subjected to a further separation step wherein the microorganisms are isolated from substantially all other material. This may be performed by centrifugation through a separation column amended with sodium hexametaphosphate at a force of about 1,000 multiples of gravity. The separation column can comprise the solutes listed previously, i.e., sucrose, CsCl, Percoll™, ficoll, metrizamide, Nycodenz™, sodium acetate, glycerol and mixtures thereof. A presently preferred solute mixture is sucrose (0.4 M) and Percoll™, in a volume ratio of about 80:20. The solute mixture is amended with about 2 mg/ml of sodium hexametaphosphate.

The microorganisms are recovered from the top layer in the centrifuge tube by membrane filtration or centrifugation and then analyzed by any suitable assay scheme. It is presently preferred to use a DNA-based detection system which amplifies a target DNA sequence which is unique to a targeted microorganism. Because sodium hexametaphosphate treatment removed environmental substances which can inhibit DNA-based systems, detection of the recovered microorganisms is unimpaired. The method of the present invention can also be used to prepare samples for other analyses such as identification by an antibody-based system or culturing on growth media.

The method of the present invention provides the following advantages: (1) greater recovery of microorganisms from environmental samples and, thus, greater detection sensitivity, and (2) recovered microorganisms are free of inhibitory substances and are, thus, detectable by DNA amplification. Sodium hexametaphosphate is stable, inexpensive, non-caustic, and non-hazardous. Compound concentration or pH during the process has been found not to affect effectiveness. With this system DNA of the microorganisms is not exposed to environmental substances that could degrade DNA integrity.

The method of the present invention can be employed for recovery of microorganisms present in clinical samples (blood, urine, sputum, skin tissue, and feces), foods and industrial products. The method requires little or no modification to accommodate those samples.

Various modifications may be made in the present invention without departing from the scope of the appended claims.

I claim:

1. A method to collect and recover microorganisms from environmental samples consisting essentially of the steps of (a) obtaining a sample for testing, (b) adding sodium hexametaphosphate to said sample, (c) centrifuging said sample containing sodium hexametaphosphate through a separation column comprising a solute containing sodium hexametaphosphate said solute selected from the group consisting of sucrose, CsCl, colloidal silica coated with polyvinyl pyrrolidone, ficoll, metrizamide, sodium acetate, glycerol and mixtures thereof, and (d) recovering any microorganism-containing material remaining above said column for analysis.

2. A method to collect and recover microorganisms from environmental samples which are not in aqueous form, consisting essentially of the steps of (a) obtaining a sample for testing, (b) suspending said sample in a suitable liquid and adding sodium hexametaphosphate thereto, (c) centrifuging said sample containing sodium hexametaphosphate through a separation column comprising a solute containing sodium hexametaphosphate said solute selected from the group consisting of sucrose, CsCl, colloidal silica coated with polyvinyl pyrrolidone, ficoll, metrizamide, sodium acetate, glycerol and mixtures thereof, and (d) recovering any microorganism-containing material remaining above said column for analysis.

3. The method of claim 2 wherein said sample is suspended in step (b) in sterile water, buffer or saline solution.

4. A method to collect and recover microorganisms from environmental samples consisting essentially of the steps of (a) obtaining a sample for testing, (b) adding sodium hexametaphosphate to said sample, (c) centrifuging said sample containing sodium hexametaphosphate at a force from about 150 to 250 multiples of gravity to remove solid sediments, insoluble salts and inert materials, (d) centrifuging the supernatant obtained in step (c) through a separation column comprising a solute containing sodium hexametaphosphate said solute selected from the group consisting of sucrose, CsCl, colloidal silica coated with polyvinyl pyrrolidone, ficoll, metrizamide, sodium acetate, glycerol and mixtures thereof, and (e) recovering any microorganism-containing material remaining above said column for analysis.

* * * * *